United States Patent [19]

Nesvadba

[11] Patent Number: 5,260,430

[45] Date of Patent: Nov. 9, 1993

[54] DIPHENYL ACETIC ACID DERIVATIVES

[75] Inventor: Peter Nesvadba, Marly, Switzerland

[73] Assignee: Ciba-Geigy Corporation, Ardsley, N.Y.

[21] Appl. No.: 980,017

[22] Filed: Nov. 23, 1992

[30] Foreign Application Priority Data

Nov. 29, 1991 [CH] Switzerland ............... 3501/91

[51] Int. Cl.$^5$ .............................. C07L 69/76
[52] U.S. Cl. ..................... 560/57; 564/171; 562/468
[58] Field of Search ............ 560/57; 562/468; 564/171

[56] References Cited

U.S. PATENT DOCUMENTS

| | | | |
|---|---|---|---|
| 4,325,863 | 4/1982 | Hinsken et al. | 624/14 |
| 4,338,244 | 7/1982 | Hinsken et al. | 524/109 |
| 5,175,312 | 12/1992 | Dubs et al. | 549/307 |

FOREIGN PATENT DOCUMENTS

| | | |
|---|---|---|
| 0146269 | 11/1984 | European Pat. Off. |
| 0182507 | 10/1985 | European Pat. Off. |
| 2034308 | 6/1980 | United Kingdom |
| 8001566 | 8/1980 | World Int. Prop. O. |

OTHER PUBLICATIONS

W. Bradley et al. J. Chem. Soc. 1622–1627 (1956).

Primary Examiner—Paul J. Killos
Attorney, Agent, or Firm—Luther A. R. Hall

[57] ABSTRACT

Novel diphenyl acetic acid derivatives of the formula I are described,

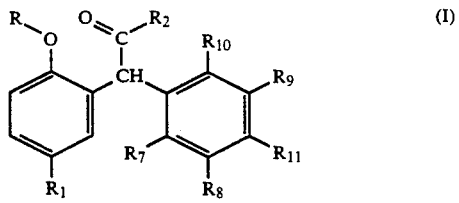

in which R is $C_3$–$C_{18}$-2-alkenyl, $C_3$–$C_8$-2-alkynyl or phenyl-$C_1$–$C_4$alkyl, each of which is unsubstituted or substituted by phenyl, $R_1$ is hydrogen, $C_1$–$C_{18}$alkyl, $C_5$–$C_{12}$cycloalkyl or phenyl-$C_1$–$C_4$alkyl, $R_2$ is —$OR_4$ or —$NR_5R_6$, $R_4$ is hydrogen, $C_1$–$C_{18}$alkyl or (—$CH_2$—)$_n$G, $R_5$ and $R_6$ independently of one another are hydrogen, $C_1$–$C_{12}$alkyl or phenyl-$C_1$–$C_4$alkyl, $R_7$, $R_8$, $R_9$ and $R_{10}$ independently of one another are hydrogen, $C_1$–$C_4$alkyl or $C_1$–$C_4$alkoxy, with the proviso that at least one of the radicals $R_7$, $R_8$, $R_9$ or $R_{10}$ is hydrogen, $R_{11}$ is hydrogen, $C_1$–$C_{18}$alkoxy, $C_5$–$C_8$cycloalkoxy, phenyl-$C_1$–$C_4$alkoxy or $C_3$–$C_{18}$-2-alkenyloxy, n is a number from 2 to 12, and G is a group of the formula

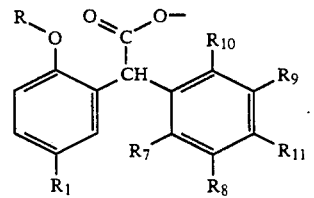

The compounds according to the invention can be used as stabilizers for organic materials.

11 Claims, No Drawings

DIPHENYL ACETIC ACID DERIVATIVES

The present invention relates to novel diphenyl acetic acid derivatives, to compositions comprising them, and to the use of the derivatives as stabilisers for organic material.

It is known to add certain chemicals to organic materials as stabilisers. These include antioxidants and processing stabilisers, which are well known to those skilled in the art.

The demand for such additives continues.

Surprisingly, it has now been found that the compounds of the formula I described below are outstandingly suitable as additives for preventing light-induced thermal and/or oxidative degradation of organic materials.

The invention therefore relates to compounds of the formula (I)

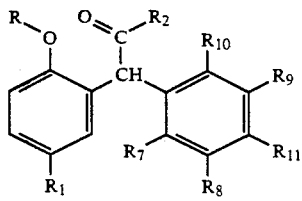

in which R is $C_3-C_{18}$-2-alkenyl, $C_3-C_8$-2-alkynyl or phenyl-$C_1-C_4$alkyl, each of which is unsubstituted or substituted by phenyl,
$R_1$ is hydrogen, $C_1-C_{18}$alkyl, $C_5-C_{12}$cycloalkyl or phenyl-$C_1-C_4$alkyl,
$R_2$ is —$OR_4$ or —$NR_5R_6$,
$R_4$ is hydrogen, $C_1-C_{18}$alkyl or (—$CH_2$—$)_nG$,
$R_5$ and $R_6$ independently of one another are hydrogen, $C_1-C_{12}$alkyl or phenyl-$C_1-C_4$alkyl,
$R_7$, $R_8$, $R_9$ and $R_{10}$ independently of one another are hydrogen, $C_1-C_4$alkyl or $C_1-C_4$alkoxy, with the proviso that at least one of the radicals $R_7$, $R_8$, $R_9$ or $R_{10}$ is hydrogen,
$R_{11}$ is hydrogen, $C_1-C_{18}$alkoxy, $C_5-C_8$cycloalkoxy, phenyl-$C_1-C_4$alkoxy or $C_3-C_{18}$-2-alkenyloxy,
n is a number from 2 to 12, and
G is a group of the formula

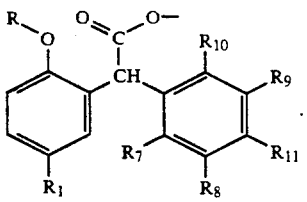

R as $C_3-C_{18}$-2-alkenyl which is unsubstituted or substituted by phenyl can be branched or unbranched and is, for example, allyl, 2-methallyl, 2-hexenyl, 2-dodecenyl, 2-tetradecenyl or 3-phenyl-2-propenyl.

R as $C_3-C_8$-2-alkinyl is derived from the alkyl radicals which have 3 to 8 C atoms and in which two C atoms are bonded by a triple bond, and is preferably propargyl.

R, $R_1$, $R_5$ and $R_6$ as phenyl-$C_1-C_4$alkyl are, for example, benzyl, phenethyl, 3-phenylpropyl, α-methylbenzyl or α,α-dimethylbenzyl. Benzyl is preferred.

If in the above formula $R_1$, $R_4$, $R_3$, $R_5$ and $R_6$ are $C_1-C_{18}$alkyl or $C_1-C_{12}$alkyl, then they are branched or unbranched radicals. Examples are methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl.

$R_1$ as $C_5-C_{12}$cycloalkyl can be, for example, cyclopentyl, cyclohexyl, cycloheptyl, cyclooctyl or cyclododecyl. Preferred compounds are cyclopentyl and cyclohexyl, in particular cyclohexyl.

If in the above formula $R_7$, $R_8$, $R_9$, $R_{10}$ and $R_{11}$ are $C_1-C_4$alkoxy or $C_1-C_{18}$alkoxy, they are branched or unbranched radicals. Examples are methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

$R_{11}$ as $C_5-C_8$cycloalkoxy is, for example, cyclopentoxy, cyclohexoxy, cycloheptoxy or cyclooctoxy.

$R_{11}$ as phenyl-$C_1-C_4$alkoxy is, for example, benzyloxy, phenethoxy, 3-phenylpropoxy, α-methylbenzyloxy or α,α-dimethylbenzyloxy. Benzyloxy is preferred.

$R_{11}$ as $C_3-C_{18}$-2-alkenyloxy can be branched or unbranched and is, for example, allyloxy, 2-methallyloxy, 2-hexenyloxy, 2-dodecenyloxy, 2-tetradecenyloxy or 3-phenyl-2-propenyloxy.

Expedient compounds of the formula I are those in which $R_7$, $R_8$, $R_9$, $R_{10}$ and $R_{11}$ are hydrogen.

Preferred compounds of the formula I are those in which
R is —$CH_2$—$CH$=$CH_2$, —$CH_2$—$C(CH_3)$=$CH_2$, —$CH_2$—$CH$=$CHR_3$, —$CH_2$—$C$≡$CH$ or phenyl-$C_1-C_4$alkyl,
$R_1$ is hydrogen or $C_1-C_8$alkyl,
$R_2$ is —$OR_4$ or —$NHR_5$,
$R_3$ is phenyl, $C_1-C_{12}$alkyl, and
$R_5$ is hydrogen, $C_1-C_4$alkyl or benzyl, and
$R_{11}$ is hydrogen, $C_1-C_{18}$alkoxy, $C_3-C_4$-2-alkenyloxy or benzyloxy.

Particularly preferred compounds of the formula I are those in which $R_1$ is methyl, t-butyl or —$C(CH_3)_2$—$CH_2$—$C(CH_3)_3$.

Compounds of the formula I in which $R_7$ and $R_{10}$ are hydrogen are of particular interest.

Especially preferred compounds of the formula I are those in which
R is unsubstituted or phenyl-substituted $C_3-C_{14}$-2-alkenyl, —$CH_2$—$C$≡$CH$ or benzyl,
$R_1$ is hydrogen or $C_1-C_8$alkyl,
$R_2$ is $OR_4$ or $NH_2$,
$R_7$ and $R_{10}$ are hydrogen,
$R_8$ and $R_9$ independently of one another are hydrogen or $C_1-C_4$alkyl, and
$R_{11}$ is hydrogen or $C_1-C_4$alkoxy.

The compounds of the formula I are outstandingly suitable for stabilising organic materials against light-induced, thermal and/or oxidative degradation. The invention therefore also relates to compositions comprising an organic material which is prone to such degradation reactions and at least one compound of the formula I, or to the use of compounds of the formula I as stabilisers for organic materials against the types of degradation which have been mentioned.

In particular, the compounds of the formula I can be used as stabilisers for natural, semisynthetic or synthetic polymers, in particular thermoplastics (mainly polyolefins) and elastomers, as well as for functional fluids, in particular lubricants and hydraulic fluids. Examples of such substrates can be found in the following list of suitable materials.

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA, LLDPE/EVA and LLDPE/EAA.

3a. Random or alternating copolymers of α-olefins with carbon monoxide.

3b. Hydrocarbon resins (for example $C_5$–$C_9$), including hydrogenated modifications thereof (for example tackifiers).

4. Polystyrene, poly(p-methylstyrene), poly(α-methylstyrene).

5. Copolymers of styrene or α-methylstyrene with dienes or acrylic derivatives, for example styrene/butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned in 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or hydroxyl-terminated polybutadienes on the one hand and aliphatic or aromatic polyisocyanates on the other, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyethers esters derived from hydroxyl-terminated polyethers; and also polyesters modified with polycarbonates or MBS.

18. Polycarbonates and polyester carbonates.
19. Polysulfones, polyether sulfones and polyether ketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Crosslinkable acrylic resins derived from substituted acrylic esters such as epoxy acrylates, urethane acrylates or polyester acrylates.
24. Alkyd resins, polyester resins or acrylate resins which are cross-linked with melamine resins, urea resins, polyisocyanates or epoxy resins.
25. Crosslinked epoxy resins which are derived from polyepoxides, for example from bisglycidyl ethers or from cycloaliphatic diepoxides.
26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.
27. Mixtures (polyblends) of the aforementioned polymers, for example PP/EPDM, polyamide/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also the mixtures of synthetic esters with mineral oils in any weight ratios which are used as spinning compositions, as well as aqueous emulsions of such materials.
29. Aqueous emulsions of natural or synthetic rubber, for example natural latex or latices of carboxylated styrene/butadiene copolymers.

The compositions according to the invention comprise expediently 0.0005 to 5, for example 0.05 to 5, preferably 0.05 to 3, but in particular 0.1 to 2, % by weight of the compounds of the formula I. There may be one or more of these compounds of the formula I, and the percentages by weight are based on the total amount of these compounds. The calculations are based on the total weight of the organic material without the compounds of the formula I.

The materials can be incorporated for example by mixing in, or applying the compounds of the formula I together with, or without, further additives by the methods conventional in the art. If they are polymers, in particular synthetic polymers, they can be incorporated before or during moulding, or by applying the dissolved or dispersed compounds to the polymer, and the solvent may subsequently be evaporated. In the case of elastomers, the latter can also be stabilised in the form of latices. A further possibility of incorporating the compounds of the formula I in polymers is adding them before, during or immediately after, the polymerisation of the corresponding monomers, or before crosslinking. The compounds of the formula I can be added as such, but also in encapsulated form (for example in waxes, oils or polymers). If the compounds of the formula I are added before or during the polymerisation, they can also act as regulators for the chain length of the polymers (chain terminators).

The compounds of the formula I or mixtures thereof can also be added to the plastics to be stabilised in the form of a master batch comprising these compounds for example at a concentration from 2.5 to 25% by weight.

The compounds of the formula I can expediently be incorporated by the following methods:
as an emulsion or dispersion (for example to latices or emulsion polymers)
as a dry mixture while mixing additives or polymer mixtures
by introducing directly in the processing apparatus (for example, inter alia, extruders and kneaders)
as a solution or melt.

Polymer compositions according to the invention can be used in a range of forms, or processed to give a range of products, for example in the form of (to give) films, fibers, small strips, moulding compositions, profiles, or as binders for surface coatings, adhesives or putties.

The invention also relates to a process for stabilising organic material, in particular thermoplastic polymers (especially polyolefins), elastomers or functional fluids against oxidative, thermal and/or light-induced degradation, which comprises adding, or applying, compounds of the formula I to this material as stabilisers.

In addition to mixtures or compounds according to the invention, the compositions according to the invention can additionally comprise further customary additives, in particular when they comprise organic, preferably synthetic, polymers. Examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butyl-hydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate.

1.4. Hydroxylated thiodiphenylethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis-(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-benzyl compounds, for example 3,5,3',5'-tetra(tert-butyl-4,4'-dihydroxydibenzyl)ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis-(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazines, for example 2,4-bis[(octylmercapto-6-(3,5-di-tert-butyl-4-hydroxyanilino)]-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauryl anilide, 4-hydroxystearyl anilide, octyl N-(3,5-di-tertbutyl-4-hydroxyphenyl)carbamate.

1.12. Esters of β-(3,5-di-tertbutyl-4-hydroxyphenyl)-propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and light stabilisers 2.1. 2-(2'-Hydroxyphenyl)benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy-, 3',5'-di-tert-amyl- or 3',5'-bis(α,α-dimethylbenzyl)- mixture of 5-chloro-3'-tert-butyl-5'-(2-octyloxycarbonylethyl)-and 5-chloro-3'-tert-butyl-5'-[2-(2ethylhexyloxy)-carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-

(2-isooctyloxycarbonylethyl)-2-hydroxyphenyl-2H-benzotriazol-2-yl, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)]-2'-hydroxyphenyl]-2H-benzotriazole with polyethylene glycol 300; [R-CH$_2$CH$_2$COO(CH$_2$)$_3$]$_2$, wherein R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, for example 4-tertbutylphenyl salicylate, phenyl salicylate, octylphenyl salicylate, dibenzoyl resorcinol, bis(4-tert-butylbenzoyl) resorcinol, benzoyl resorcinol, the 2,4-di-tertbutylphenyl ester of 3,5-di-tert-butyl-4-hydroxybenzoic acid, hexadecyl 3,5-di-tert-butyl-4-hydroxybenzoate, octadecyl 3,5-di-tert-butyl-4-hydroxybenzoate, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], e.g. the 1:1- or 1:2 complex, with or without additional ligands, typically n-butylamine, triethanolamine or N-cyclohexyl-diethanolamine, nickel dibutyl dithiocarbamate, nickel salts of monoalkyl esters, typically methyl or ethyl esters, of 4-hydroxy-3,5-di-tert-butylbenzylphosphonic acid, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, the bis(1,2,2,6,6-pentamethylpiperidyl) ester of n-butyl-3,5-di-tert-butyl-4-hydroxybenzylmalonic acid, the condensate of 1-hydroxyethyl-2,2,6,6-tetramethyl-4-hydroxypiperidine and succinic acid, the condensate of N,N'-bis(2,2,6,6-tetramethyl-4-piperidyl)-hexamethylenediamine and 4-tertoctylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspriro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis-(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxypropoxy)-phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bis(phenylhydrazide), N,N'-diacetaladipic acid dihydrazide, N,N'-bis(salicyloy)oxalic acid dihydrazide, N,N'-bis(salicyloyl)thiopropionic acid dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, bis(2,6-di-tert-butyl-4-methylphenyl)pentaerythritol diphosphite, bis(isodecyloxy)pentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine.

5. Compounds which decompose peroxide, for example esters, typically the lauryl, stearyl, myristyl or tridecyl esters, of β-thiodipropionic acid, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluores-cent whitening agents, flameproofing agents, antistatic agents and blowing agents.

The costabilisers are added for example at concentrations of 0.01 to 10% relative to the total weight of the material to be stabilised.

The compounds of the formula I according to the invention can be used in particular together with phenolic antioxidants. The compositions according to the invention therefore preferably comprise, besides compounds of the formula I, phenolic antioxidants, in particular such antioxidants as have been listed in the above items 1.1 to 1.16.

Other preferred compositions comprise, besides the compounds of the formula I, at least one organic phosphite or phosphonite.

As already emphasised, the compounds according to the invention are used particularly advantageously as stablisers in polyolefins, mainly as thermostabilisers. Excellent stabilising is obtained for example when they are used in combination with organic phosphites or phosphonites. The compounds according to the invention have the advantage of being effective in exceedingly small amounts. They are used, for example, in amounts from 0.0001 to 0.015, in particular 0.0001 to 0.008, % by weight based on the polyolefin. The organic phosphite or phosphonite is expediently used in an amount of 0.01 to 2, in particular 0.01 to 1, % by weight, also based on the polyolefin. Organic phosphites or phosphonites which are preferably used are such organic phosphites or phosphonites as have been described in German Patent Application P 4 202 276.2. In this publication, see, in particular, the patent claims, the examples and pages 5, last paragraph, to page 11. Particularly expedient phosphites and phosphonites can also be found in item 4 of the above list of costabilisers.

The present invention also relates to the use of compounds of the formula I for stabilising organic material sensitive to oxidative, thermal and/or light-induced degradation, in particular natural or (semi)synthetic polymers, mainly thermoplastic polymers or elastomers and, very particularly, as processing stabilisers for thermoplastic polymers.

Expedient and preferred compounds of the formula I as described above give expedient and preferred compositions.

The preparation of the compounds according to the invention starts from, for example, benzofuranones of the formula II, whose preparation is described in U.S. Pat. Nos. 4,325,863 and 4,338,244. Reaction with ammonia or primary or secondary amines $HNR_5R_6$ gives amides of the formula III which can be reacted with organic halides R-Hal(Hal=halogen, preferably chlorine) to give amides of the formula IV. The latter can be converted into acids of the formula V, for example using bases or mineral acids, and these acids of the formula V can be esterified by known methods (for example by reaction with alcohols of the formula $R_4OH$ where $R_4 \neq H$ to give compounds of the formula I where $R_2 = OR_4$ ($R_4 \neq H$)

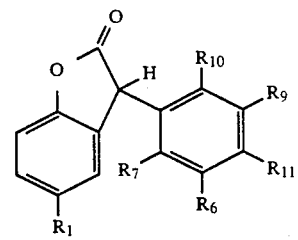

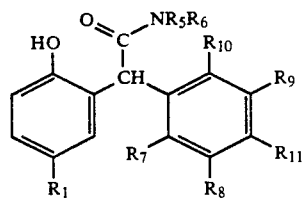

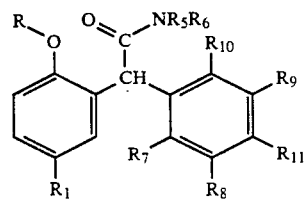

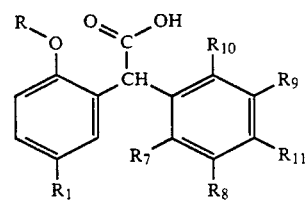

As already mentioned, the compounds of the formula II can be prepared in a manner known per se.

For example, and this is preferred, a phenol of the formula VI

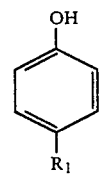

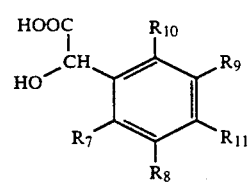

in which $R_1$ has the abovementioned meaning is reacted with a mandelic acid derivative substituted in the phenol ring, of the formula VII in which $R_7$, $R_8$, $R_9$, $R_{10}$ and $R_{11}$ are as defined above, at elevated temperature, in particular temperatures from 130° to 200° C., in the melt or in a solvent, if appropriate under a moderately subatmospheric pressure, to give compounds of the formula II. The reaction is preferably carried out in a solvent, for example acetic acid, propionic acid or formic acid, in a temperature range from 50° to 130° C. The reaction can be catalysed by addition of an acid such as hydrochloric acid, sulfuric acid or methanesulfonic acid.

The mandelic acid substituted in the phenyl ring, of the formula VII, are known from the literature or can be prepared in an analogous manner, for example by the method of W. Bradley et al, J. Chem. Soc. 1956, 1622; EP-A-146 269, Ep-B-182 507 (Example 1, page 4) or DE-A-2 944 295.

The examples which follow illustrate the invention in greater detail. Parts and percentages are by weight.

EXAMPLE 1

Preparation of N-2-(2-allyloxy-5-tert-butylphenyl)-2-phenylacetamide (compound (101), Table 1)

A solution of 53.26 g (0.20 mol) of 5-tert-butyl-3-phenylbenzofuran-2-one in 100 ml of tetrahydrofuran is treated with 18 ml of 25% aqueous ammonia solution, and the mixture is stirred at room temperature for approx. 2.5 hours. 600 ml of water are subsequently added, and the solid which has precipitated is filtered. The residue is washed with water and dried. 56.7 g (20%) of N-2-(2-hydroxy-5-tert-butylphenyl)-2-phenylacetamide.

23.6 g (83 mmol) of N-2-(2-hydroxy-5-tert-butylphenyl)-2-phenylacetamide are added to a sodium acylate solution prepared by adding 2.3 g (110 mmol) of sodium to 200 ml of ethanol, and, after everything has dissolved, 13.8 g (110 mmol) of allyl bromide are added, and the mixture subsequently kept at 50° C. for approx. 4.5 hours. The reaction mixture is concentrated on a vacuum rotary evaporator, the residue is taken up in methylene chloride, the mixture is filtered, and the product is reconcentrated on a vacuum rotary evaporator. Crystallisation of the residue from ethyl acetate/ligroin (1:1) gives 22.3 g (83%) of 2-(2-allyloxy-5-tert-butylphenyl)-2-phenylacetamide, m.p. 172°–174° C. (Compound (101), Table 1).

Analogously to Example 1, compounds are prepared from the corresponding benzofuran-2-ones of the formula II, for example 5-(1,1,3,3-tetramethylbutyl)-3-phenyl-benzofuran-2-one, 3-(4-ethoxy-phenyl)-5-methyl-benzofuran-2-one or 5-tert-butyl-3-(3,5-dimethyl-4-methoxy-phenyl)-benzofuran-2-one, and alkyl halides, for example 3-bromo-1-phenyl-1-propene, benzyl chloride, CH₃(CH₂)₁₀—CH=CH—CH₂Br [prepared from CH₃(CH₂)₁₀—CH=CH—CH₃ with N-bromosuccinimide in carbon tetrachloride] or propargyl chloride, the compounds (102), (103), (104), (108), (109), (111) and (112).

Preparation of benzofuran-2-ones of the formula II:

A mixture of 1.50 mol of a phenol, for example 4-tert-butylphenol, 4-(1,1,3,3-tetramethylbutyl)phenol or 4-methyl-phenol, and 1.0 mol of a mandelic acid is stirred for 2 hours at 140°–150° C. under nitrogen atmosphere. Stirring is subsequently continued under a slight subatmospheric pressure (50 mbar) for a further 1.5 hours at 150° C. The excess phenol is distilled off under a high vacuum. Crystallisation of the residue from xylene/ethanol gives the benzofuran-2-ones of the formula II, for example 5-tert-butyl-3-phenyl-benzofuran-2-one, m.p. 134°–135° C. (84%), 5-(1,1,3,3-tetramethylbutyl)-3-phenyl-benzofuran-2-one, resin, (chromatography on silica gel using the eluent system dichloromethane/hexane 1:1) (46%), 3-(4-ethoxy-phenyl)-5-methyl-benzofuran-2-one, m.p. 80°–83° C. (59%) or 5-tert-butyl-3-(3,5-dimethyl-4-methoxy-phenyl)-benzofuran-2-one, m.p. 121°–123° C. (44%).

Preparation of substituted mandelic acids:

20.8 g (0.10 mol) of sodium 4-hydroxymandelate monohydrate and 6.6 g (0.10 mol) of potassium hydroxide are dissolved in 75 ml of methanol together with 1.0 g (6.7 mmol) of sodium iodide. 0.12 mol of alkyl bromide are then added (in the case of methallyl, methallyl chloride is used), and the mixture is refluxed for 16 hours under a nitrogen atmosphere. The reaction mixture is concentrated on a vacuum rotary evaporator, and the residue is acidified using concentrated hydrochloric acid. The product is extracted three times using butyl acetate. The organic phases are washed with water, combined, dried over sodium sulfate and concentrated on a vacuum rotary evaporator. Crystallisation of the residue from toluene/petroleum spirit gives the 4-alkoxymandelic acids, for example 4-methallyloxymandelic acid, m.p. 121°–126° C. (65%); 4-n-tetradecyloxymandelic acid m.p. 104°–107° C. (68%); 4-n-octoxymandelic acid, m.p. 96°–99° C. (58%); 4-n-hexoxymandelic acid, m.p. 103°–106° C. (69%); 4-n-octadecyloxymandelic acid, m.p. 103°–109° C. (29%), 4-n-butoxymandelic acid, m.p. 132°–134° C. (67%) or 4-ethoxymandelic acid, m.p. 127°–129° C. (89%).

Preparation of 4-benzyloxymandelic acid:

A solution of 41.6 g (0.20 mol) of sodium 4-hydroxymandelate monohydrate, 9.6 g (0.24 mol) of sodium hydroxide and 27.9 g (0.22 mol) of benzyl chloride in 50 ml of water is stirred for 17 hours at 70° C. It is then diluted using 50 ml of water, and a further 4.0 g (0.10 mol) of sodium hydroxide are added. The reaction mixture is refluxed for one hour, then cooled and acidified using concentrated hydrochloric acid, and the product which has precipitated is filtered. The residue is washed with cold water and subsequently dried under a high vacuum. 35.6 g (69%) of 4-benzyloxymandelic acid, m.p. 148°–155° C., result.

Preparation of 4-alkoxy-3,5-dimethylmandelic acids:

0.0375 mol of dialkyl sulfate are added dropwise in the course of approx. 15 minutes to a solution, stirred at 100° C., of 4.9 g (0.025 mol) of 3,5-dimethyl-4-hydroxymandelic acid and 3.0 g (0.075 mol) of sodium hydroxide in 10 ml of water. Stirring of the reaction mixture is then continued for a further hour at 100° C. After cooling, the mixture is acidified using concentrated hydrochloric acid, and the product which has precipitated is extracted twice using approx. 30 ml of ethyl acetate in each case. The organic phases are washed with water, combined, dried over sodium sulfate and concentrated on a vacuum rotary evaporator. The 4-alkoxy-3,5-dimethylmandelic acids, for example 3,5-dimethyl-4-methoxymandelic acid, m.p. 134°–136° C. (83%) or 4-ethoxy-3,5-dimethylmandelic acid, resin (81%), result.

Preparation of substituted 4-hydroxymandelic acids:

0.30 mol of starting phenol are dissolved under nitrogen atmosphere in 150 ml of 2N sodium hydroxide solution. After the mixture has been cooled to +5° C., 4.8 g (0.12 mol) of sodium hydroxide and 13.3 ml (0.12 mol) of 50% aqueous glyoxylic acid are added, and the reaction mixture is stirred for 4 hours at room temperature. After in each case 4 hours, two additions of a further 0.12 mol of sodium hydroxide and glyoxylic acid are made (0.36 mol in total). The reaction mixture is subsequently stirred for a further 12 hours, then neutralised using concentrated hydrochloric acid and washed using two 75 mol portions of petroleum ether.

The aqueous phase is now acidified using concentrated hydrochloric acid and extracted several times using ether. The organic phases are combined, dried over magnesium sulfate and concentrated on a vacuum rotary evaporator. In this way, the following products are obtained: 3,5-dimethyl-4-hydroxymandelic acid, m.p. 132°-135° C. (85%); 4-hydroxy-3-methylmandelic acid, m.p. 115°-120° C., (55%); 4-hydroxy-3-tert-butylmandelic acid, m.p. 156°-158° C., (26%); and 3-isopropyl-4-hydroxy-2-methylmandelic acid, m.p. 114°-119° C., (20%).

EXAMPLE 2

Preparation of 2-(2-allyloxy-5-tert-butylphenyl)-2-phenylacetic acid (compound (105), Table 1)

A suspension of 18.4 g (57.0 mmol) of N-2-(2-allyloxy-5-tert-butylphenyl)-2-phenylacetamide (compound (101), Table 1, Example 1) and 30 g (0.54 mol) of potassium hydroxide in 70 ml of methanol is refluxed for 57 hours. The suspension is subsequently diluted with 150 ml of water, and the methanol is evaporated on a vacuum rotary evaporator. The aqueous residue is poured into a solution of 20 ml of concentrated sulfuric acid in 500 ml of water. The product which has precipitated is extracted using dichloromethane. The organic phases are washed with water, combined, dried over magnesium sulfate and concentrated on a vacuum rotary evaporator. Crystallisation of the residue from ligroin yields 15.3 g (83%) of 2-(2-allyloxy-5-tert-butylphenyl)-2-phenylacetic acid, m.p. 120°-122° C. (compound 105), Table 1).

Analogously to Example 2, compound (110) is obtained starting from compound (109).

EXAMPLE 3

Preparation of stearyl 2-(2-allyloxy-5-tert-butylphenyl)-2-phenylacetate (compound (106), Table 1)

A solution of 3.24 g (10.0 mmol) of 2-(2-allyloxy-5-tert-butylphenyl)-2-phenylacetic acid (compound (105), Example 2) and 2.70 g (10.0 mmol) of stearyl alcohol (1-octadecanol) in 25 mol of dichloromethane is treated with 100 mg (0.82 mmol) of 4-dimethylaminopyridine and 2.20 g (10.7 mmol) of N,N'-dicyclohexylcarbodiimide, and the mixture is stirred for 60 hours at room temperature. The reaction mixture is filtered and concentrated on a vacuum rotary evaporator. Chromatography of the residue from silica gel using the diluent system dichloromethane/hexane=1:1 yields 4.0 g (69%) of stearyl 2-(2-allyloxy-5-tert-butylphenyl)-2-phenylacetate (compound (106), Table 1) as an oil.

Compound (107) is prepared analogously to Example 3, except that half an equivalent of 1,2-dodecanediol is used instead of stearyl alcohol.

TABLE 1

| No. | Compound | M.p. (°C.) | C (%), (calculated/found) | H (%). | N (%) | Yield (%) |
|---|---|---|---|---|---|---|
| 101 | 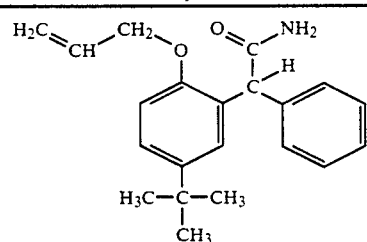 | 172-174 | 77.98<br>77.61 | 7.79<br>7.78 | 4.33<br>4.22 | 83 |
| 102 | 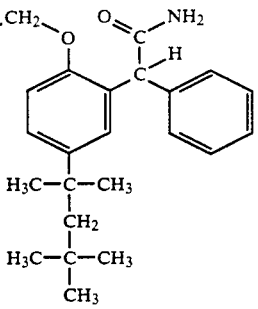 | 75-78 | 79.11<br>78.90 | 8.76<br>8.96 | 3.69<br>3.43 | 87 |
| 103 | 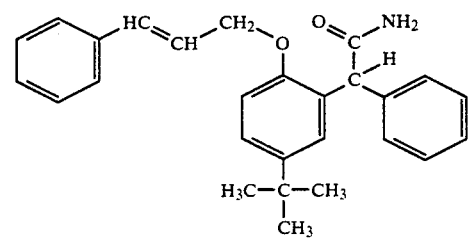 | 165-168 | 81.17<br>81.16 | 7.32<br>7.34 | 3.51<br>3.34 | 86 |

TABLE 1-continued

| No. | Compound | M.p. (°C.) | C (%), H (%), N (%) (calculated/found) | | | Yield (%) |
|---|---|---|---|---|---|---|
| 104 | n-$C_{11}H_{23}$—HC=CH—$CH_2$—O— ... (2-phenyl-2-[2-(tridec-2-enyloxy)-5-tert-butylphenyl]acetamide) | Wax | Characterised by $^1$H-NMR in CDCl$_3$ $\delta$(H*) = 5.32 ppm | | | 55 |
| 105 | $H_2C$=CH—$CH_2$—O— ... (2-(2-allyloxy-5-tert-butylphenyl)-2-phenylacetic acid) | 120–122 | 77.75 77.59 | 7.46 7.58 | — — | 83 |
| 106 | $H_2C$=CH—$CH_2$—O— ... —O-n-$C_{18}H_{37}$ | Oil | 81.20 81.10 | 10.48 10.64 | — — | 69 |
| 107 | [$H_2C$=CH—$CH_2$—O— ... —O—$(CH_2)_6$—]$_2$ | Oil | Characterised by $^1$H-NMR in CDCl$_3$ $\delta$(H*) = 5.34 ppm | | | 69 |
| 108 | HC≡C—$CH_2$—O— ... $CONH_2$ | 135–138 | 78.47 78.38 | 7.21 7.35 | 4.36 4.10 | 86 |
| 109 | PhCH$_2$—O— ... $CONH_2$ | 154–156 | 80.40 80.17 | 7.29 7.24 | 3.75 3.63 | 66 |

TABLE 1-continued

| No. | Compound | M.p. (°C.) | C (%), H (%), N (%) (calculated/found) | | | Yield (%) |
|---|---|---|---|---|---|---|
| 110 | [structure: 2-benzyloxy-5-tert-butylphenyl phenyl acetic acid] | 124–127 | 80.18 80.20 | 7.00 6.91 | — — | 75 |
| 111 | [structure: 2-allyloxy-5-methylphenyl (4-ethoxyphenyl) acetamide] | 117–119 | 73.82 73.89 | 7.12 7.01 | 4.30 4.19 | 81 |
| 112 | [structure: 2-allyloxy-5-tert-butylphenyl (3,5-dimethyl-4-methoxyphenyl) acetamide] | 101–103 | 75.56 75.53 | 8.19 8.27 | 3.67 3.51 | 88 |

EXAMPLE 4

Stabilisation of polypropylene for multiple extrusion 1.3 kg of polypropylene powder (Profax® 6501) (melt index 3.4 g/10 min, measured at 230° C. using 2.16 kg) are mixed with 0.05% of calcium stearate, 0.05% of pentaerythritol β-(3,5-di-tert-butyl-4-hydroxyphenyl)-propionate Irganox® 1010 (Ciba-Geigy) and 0.05% of the compound of Table 1. In an extruder having a cylinder diameter of 20 mm and a length of 400 mm, this mixture is extruded at 100 rpm, the following temperatures being set in the three heating zones: 260° C., and 270° C. For cooling, the extrudate is passed through a water bath and subsequently granulated. After two further extrusions which proceed in the same manner, the melt index is measured (at 230° C. using 2.16 kg). A great increase in melt index signifies substantial chain degradation, i.e. poor stability.

The results are compiled in Table 2 below:

TABLE 2

| Compound from Table 1 | Melt index after 3 extrusions |
|---|---|
| — | 23.0 |
| 101 | 6.0 |
| 102 | 6.3 |
| 103 | 6.0 |
| 104 | 6.3 |
| 105 | 5.0 |
| 106 | 6.5 |
| 107 | 8.3 |
| 108 | 8.6 |

What is claimed is:

1. A compound of the formula I

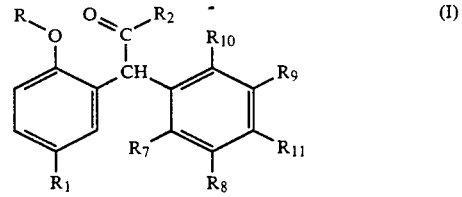

in which R is $C_3$-$C_{18}$-2-alkenyl, $C_3$-$C_8$-2-alkynyl or phenyl-$C_1$-$C_4$alkyl, each of which is unsubstituted or substituted by phenyl, $R_1$ is hydrogen, $C_1$-$C_{18}$alkyl, $C_5$-$C_{12}$cycloalkyl or phenyl-$C_1$-$C_4$alkyl, $R_2$ is —$OR_4$ or —$NR_5R_6$, $R_4$ is hydrogen, $C_1$-$C_{18}$alkyl or (—$CH_2$—$)_nG$, $R_5$ and $R_6$ independently of one another are hydrogen, $C_1$-$C_{12}$alkyl or phenyl-$C_1$-$C_4$alkyl, $R_7$, $R_8$, $R_9$ and $R_{10}$ independently of one another are hydrogen, $C_1$-$C_4$alkyl or $C_1$-$C_4$alkoxy, with the proviso that at least one of the radicals $R_7$, $R_8$, $R_9$ or $R_{10}$ is hydrogen, $R_{11}$ is hydrogen, $C_1$-$C_{18}$alkoxy, $C_5$-$C_8$cycloalkoxy, phenyl-$C_1$-$C_4$alkoxy or $C_3$-$C_{18}$-2-alkenyloxy, n is a number from 2 to 12, and G is a group of the formula

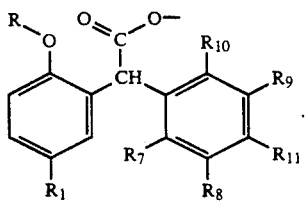

2. A compound according to claim 1, in which $R_7$, $R_8$, $R_9$, $R_{10}$ and $R_{11}$ are hydrogen.

3. A compound according to claim 1, in which R is —$CH_2$—$CH$=$CH_2$, —$CH_2$—$C(CH_3)$=$CH_2$, —$CH_2$—$CH$=$CHR_3$, —$CH_2$—$C$≡$CH$ or phenyl-$C_1$-$C_4$alkyl, $R_1$ is hydrogen or $C_1$-$C_8$alkyl,
$R_2$ is —$OR_4$ or —$NHR_5$,
$R_3$ is phenyl, $C_1$-$C_{12}$alkyl, and
$R_5$ is hydrogen, $C_1$-$C_4$alkyl or benzyl, and
$R_{11}$ is hydrogen, $C_1$-$C_{18}$alkoxy, $C_3$-$C_4$-2-alkenyloxy or benzyloxy.

4. A compound according to claim 1, in which $R_1$ is methyl, t-butyl or —$C(CH_3)_2$—$CH_2$—$C(CH_3)_3$.

5. A compound according to claim 1, in which $R_7$ and $R_{10}$ are hydrogen.

6. A compound according to claim 1, in which
R is unsubstituted or phenyl-substituted $C_3$-$C_{14}$-2-alkenyl, —$CH_2$—$C$≡$CH$ or benzyl,
$R_1$ is hydrogen or $C_1$-$C_8$alkyl,
$R_2$ is $OR_4$ or $NH_2$,
$R_7$ and $R_{10}$ are hydrogen,
$R_8$ and $R_9$ independently of one another are hydrogen or $C_1$-$C_4$alkyl, and
$R_{11}$ is hydrogen or $C_1$-$C_4$alkoxy.

7. A composition comprising
a) an organic material subjected to oxidative, thermal or light-induced degradation, and
b) at least one compound of the formula I according to claim 1.

8. A composition according to claim 7, in which component a) is a synthetic polymer.

9. A composition according to claim 7, in which component b) is present in an amount from 0.0005 to 5% based on the weight of component a).

10. A composition according to claim 7, additionally comprising an organic phosphite or phosphonite.

11. A process for stabilising an organic material against oxidative, thermal or light-induced degradation, which comprises incorporating or applying at least one compound of the formula I defined in claim 1 into, or onto, respectively, this organic material.

* * * * *